(12) United States Patent
Malek

(10) Patent No.: US 9,962,444 B2
(45) Date of Patent: *May 8, 2018

(54) PHARMACOKINETICALLY EXTENDED ACTION TOPICAL HAIR GROWTH FORMULATION, AND ADMINISTRATION METHOD

(71) Applicant: Shane Malek, Henderson, NV (US)

(72) Inventor: Shane Malek, Henderson, NV (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/277,260

(22) Filed: Sep. 27, 2016

(65) Prior Publication Data

US 2018/0085464 A1 Mar. 29, 2018

(51) Int. Cl.
| | | |
|---|---|---|
| A61K 47/10 | (2017.01) |
| A61K 31/506 | (2006.01) |
| A61K 47/22 | (2006.01) |
| A61K 47/14 | (2017.01) |
| A61K 47/46 | (2006.01) |
| A61K 47/20 | (2006.01) |

(52) U.S. Cl.
CPC ............ *A61K 47/10* (2013.01); *A61K 31/506* (2013.01); *A61K 47/14* (2013.01); *A61K 47/20* (2013.01); *A61K 47/22* (2013.01); *A61K 47/46* (2013.01)

(58) Field of Classification Search
None
See application file for complete search history.

(56) References Cited

U.S. PATENT DOCUMENTS

| | | |
|---|---|---|
| 3,215,602 A | 11/1965 | Diamond |
| 3,306,824 A | 2/1967 | Laasko et al. |
| 3,317,380 A | 5/1967 | Veldkamp |
| 3,427,382 A | 2/1969 | Haefele |
| 3,729,568 A | 4/1973 | Kligman |
| 4,021,574 A | 5/1977 | Bollag et al. |
| 4,034,114 A | 7/1977 | Yu et al. |
| 4,139,619 A | 2/1979 | Chidsey, III |
| 4,170,229 A | 10/1979 | Olson |
| 4,185,099 A | 1/1980 | Sorbini |
| 4,201,235 A | 5/1980 | Ciavatta |
| 4,405,525 A | 9/1983 | Knight et al. |
| 4,820,512 A | 4/1989 | Grollier |
| 4,855,294 A | 8/1989 | Patel et al. |
| 5,030,442 A | 7/1991 | Uster et al. |
| 5,183,817 A | 2/1993 | Bazzano |
| 5,270,035 A | 12/1993 | Chimento |
| 5,514,672 A | 5/1996 | Bazzano |
| 5,733,572 A | 3/1998 | Unger et al. |
| 5,750,108 A | 5/1998 | Edwards |
| 5,800,807 A | 9/1998 | Hu et al. |
| 5,824,295 A | 10/1998 | Syed et al. |
| 5,834,014 A | 11/1998 | Weiner et al. |
| 5,843,415 A | 12/1998 | Klar |
| 5,853,706 A | 12/1998 | Klar |
| 5,917,021 A | 6/1999 | Lee |
| 5,951,991 A | 9/1999 | Wagner et al. |
| 5,972,345 A | 10/1999 | Chizick et al. |
| 6,156,295 A | 12/2000 | Shah |
| 6,255,313 B1 | 7/2001 | Suzuki et al. |
| 6,284,234 B1 | 9/2001 | Niemiec et al. |
| 6,379,688 B2 | 4/2002 | Yamaguchi et al. |
| 6,589,514 B2 | 7/2003 | Jensen et al. |
| 6,596,266 B2 | 7/2003 | Catalfo et al. |
| 6,723,309 B1 | 4/2004 | Deane |
| 6,946,120 B2 | 9/2005 | Wai-Chiu So et al. |
| 7,310,141 B2 | 12/2007 | Uda et al. |
| 7,749,489 B2 | 7/2010 | Malek |
| 8,119,111 B2 | 2/2012 | Malek |
| 8,147,815 B2 | 4/2012 | Malek |
| 8,156,295 B2 | 4/2012 | Singer |
| 8,372,383 B2 | 2/2013 | Dascalu |
| 8,444,960 B2 | 5/2013 | Malek |
| 2001/0031286 A1 | 10/2001 | Porras et al. |
| 2002/0009423 A1 | 1/2002 | Murad |
| 2002/0048558 A1 | 4/2002 | Niemiec et al. |
| 2002/0053537 A1 | 5/2002 | Lucido et al. |
| 2003/0007941 A1 | 1/2003 | Cornelius et al. |
| 2003/0053971 A1 | 3/2003 | Carson et al. |

(Continued)

FOREIGN PATENT DOCUMENTS

| | | |
|---|---|---|
| JP | 64-56610 A | 3/1989 |
| JP | 1-242516 A | 9/1989 |
| JP | 02-297006 A | 12/1990 |
| JP | 05-215532 A | 8/1993 |
| JP | 2006-22091 A | 1/2006 |
| WO | 9325168 A1 | 12/1993 |
| WO | 9702041 A1 | 1/1997 |
| WO | 9953923 A1 | 10/1999 |
| WO | 0007627 A2 | 2/2000 |
| WO | 02011698 A1 | 2/2002 |
| WO | 03055454 A1 | 7/2003 |

OTHER PUBLICATIONS

Ashton, P., et al., "Effects of Surfactants in Percutaneous Absorption", "Pharmaceutica Acta Helvetiae", 1986, pp. 228-235, vol. 61, No. 8.

(Continued)

*Primary Examiner* — Shirley V Gembeh
(74) *Attorney, Agent, or Firm* — Hultquist, PLLC; Steven J. Hultquist

(57) ABSTRACT

A method of inducing hair growth by topical administration of minoxidil is described, including topically applying minoxidil to a skin region susceptible to induction of hair growth, wherein the applied minoxidil is administered to the skin region (i) in a formulation comprising a release composition that mediates a dermal flux of minoxidil of at least 1.5 μg minoxidil/cm² skin area/hour for a time of from 17 to 27 hours, at an applied dose of from 2 to 20 mg minoxidil to said skin region, and with a period of from 16 to 30 hours before any subsequent reapplication of the formulation, or (ii) subsequent to administration to the skin region of said release composition so that the sequentially applied minoxidil and release composition together mediate the dermal flux of minoxidil of at least 1.5 μg minoxidil/cm² skin area/hour for a time of from 17 to 27 hours, at an applied dose of from 2 to 20 mg minoxidil to said skin region, and with a period of from 16 to 30 hours before any subsequent sequential reapplication of the minoxidil and release composition.

26 Claims, 1 Drawing Sheet

(56) References Cited

U.S. PATENT DOCUMENTS

| | | |
|---|---|---|
| 2003/0077297 A1 | 4/2003 | Chen et al. |
| 2003/0092754 A1 | 5/2003 | Nishimuta et al. |
| 2003/0199644 A1 | 10/2003 | Kim et al. |
| 2004/0096420 A1 | 5/2004 | Catalfo et al. |
| 2004/0141935 A1 | 7/2004 | Styczynski et al. |
| 2004/0157766 A1 | 8/2004 | Embil et al. |
| 2004/0204433 A1 | 10/2004 | Imamura et al. |
| 2004/0254252 A1 | 12/2004 | Engles et al. |
| 2005/0049232 A1 | 3/2005 | Lindau |
| 2005/0079139 A1 | 4/2005 | Jacques et al. |
| 2005/0163811 A1 | 7/2005 | Lee et al. |
| 2005/0186164 A1 | 8/2005 | Akyuz |
| 2005/0238675 A1 | 10/2005 | Li et al. |
| 2007/0141004 A1 | 6/2007 | Malek |
| 2007/0141015 A1 | 6/2007 | Malek |
| 2011/0189114 A1 | 8/2011 | Maniga |
| 2013/0096203 A1 | 4/2013 | Kulesza |

OTHER PUBLICATIONS

Chiang, C., et al., "Bioavailability Assessment of Topical Delivery Systems: Effect of Inter-Subject Variability on Relative In Vitro . . . ", "International Journal of Pharmaceutics", Feb. 15, 1989, pp. 21-26, vol. 50, No. 1.

Colo, G., et al., "Influence of Drug-Surfactant and Skin-Surfactant Interactions on Percutaneous Absorption of Two Model Compounds From . . . ", "International Journal of Pharmaceutics", Feb. 15, 1989, pp. 27-34, vol. 50, No. 1.

Dethlefs, J., et al., "Effect of a Combination of Vitamin and Amino Acid on the Hair Growth", "Zeitschrift fur Allgemeinmedizin (German)", Apr. 30, 1977, pp. 684-688, vol. 53, No. 12.

Dethlefs, J., et al., "Effect of a Combination of Vitamin and Amino Acid on the Hair Growth", "Zeitschrift fur Allgemeinmedizin (German)", Apr. 30, 1977, pp. 684-688 (English Abstract), vol. 53, No. 12.

Fisher, A., "Use of Glycerin in Topical Minoxidil Solutions for Patients Allergic to Propylene Glycol", "Cutis", Feb. 1990, pp. 81-82, vol. 45, No. 2.

Fragrance Journal, "Fragrance Journal", Aug. 25, 2001, pp. 364-373 (Including English Translation of Tables 2 and 3), vol. 1, No. 1.

Much, T., "Treatment of Alopecia Areata With Vitamin A Acid", "Zeitschrift fur Hautkrankheiten (German)", Dec. 1, 1976, pp. 993-998, vol. 51, No. 23.

Much, T., "Treatment of Alopecia Areata With Vitamin A Acid", "Zeitschrift fur Hautkrankheiten (German)", Dec. 1, 1976, pp. 993-998 (English Abstract), vol. 51, No. 23.

Olsen, E., et al., "A Randomized Clinical Trial of 5% Topical Minoxidil Versus 2% Topical Minoxidil and Placebo in the Treatment of . . . ", "Journal of American Academy of Dermatology", Sep. 2002, pp. 377-385, vol. 47, No. 3.

Rook, A., "Some Chemical Influences on Hair Growth and Pigmentation", "The British Journal of Dermatology", Mar. 1965, pp. 115-129, vol. 77, No. 3.

Sarpotdar, P., et al., "Percutaneous Absorption Enhancement by Nonionic Surfactants", "Drug Development and Industrial Pharmacy", Jan. 1, 1986, pp. 1625-1631, vol. 12, No. 11-13.

Sawaya, M., "Novel Agents for the Treatment of Alopecia", "Seminars in Cutaneous Medicine and Surgery", Dec. 1998, pp. 276-283, vol. 17, No. 4.

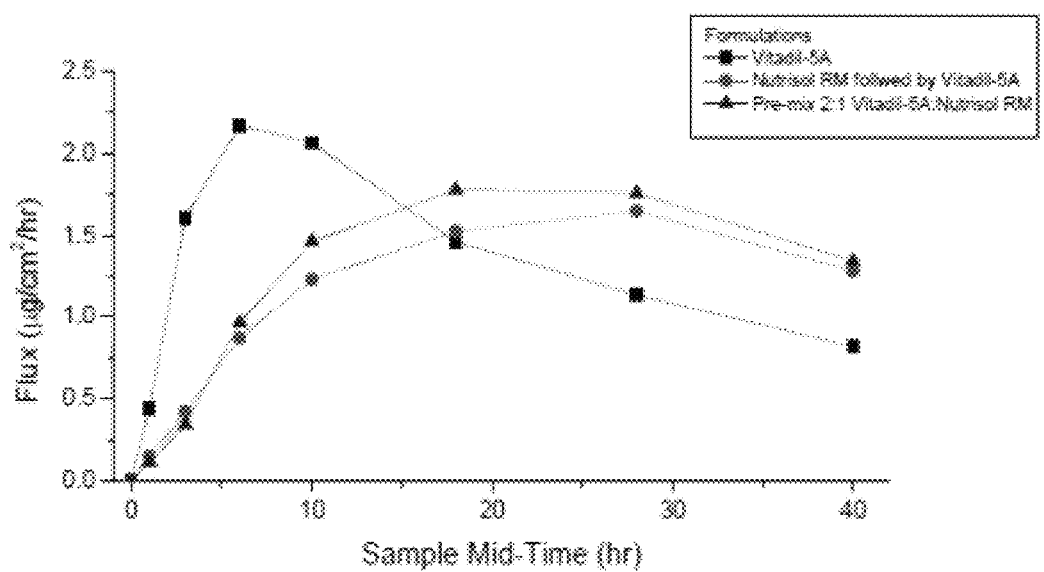

PHARMACOKINETICALLY EXTENDED ACTION TOPICAL HAIR GROWTH FORMULATION, AND ADMINISTRATION METHOD

FIELD

The present disclosure relates to topical hair growth formulations for administration to scalp areas for promotion of hair growth on the treated scalp areas, and to methods of making and using such formulations.

DESCRIPTION OF THE RELATED ART

U.S. Pat. No. 7,749,489, issued Jul. 6, 2010 in the name of Shane Malek for "Topical Administration Carrier Composition and Therapeutic Formulations Comprising Same," describes topical hair growth compositions containing active ingredient such as minoxidil, which are formulated to retard evaporative losses of solvent component(s) from the administered composition and systemic migration losses of the active ingredient in the composition. This patent addresses the problem of systemic migration associated with 5% minoxidil compositions, including incidence of heart palpitations and scalp irritation, and the achievement of reduction in such unwanted side effects, by use of a carrier comprising water, glycerin, and polysorbate with which the minoxidil active ingredient is delivered to the scalp by topical administration.

The '489 patent teaches the application to the scalp of the minoxidil-containing formulations twice-daily, in an amount of 0.5-2 mL of the formulation in each administration, so that 30 mg per day of the active minoxidil ingredient is delivered to the scalp by the twice-daily administration. Such patent also describes the administration regimen that is conventionally used for minoxidil-containing formulations commercially available under the Rogaine® trademark, as being a 1 mL 2% b.i.d. (Latin, "bis in die", or twice a day) dose, with a 5 mg starting dose, and a 30 mg/day steady-state dose (15 mg twice daily). The '489 patent also describes 5% minoxidil Rogaine® formulations.

The art continues to seek improvements in hair growth products, including those containing minoxidil as the active ingredient, since topical minoxidil-containing hair growth formulations have proven beneficial for inducing hair growth on scalp regions that are bald or balding, or that otherwise are characterized by thin or thinning hair.

SUMMARY

The present disclosure relates to a method of inducing hair growth by topical administration of minoxidil.

In one aspect, the disclosure relates to a method of inducing hair growth by topical administration of minoxidil, said method comprising topically applying minoxidil to a skin region susceptible to induction of hair growth, wherein the applied minoxidil is administered to the skin region (i) in a formulation comprising a release composition that mediates a dermal flux of minoxidil of at least 1.5 μg minoxidil/cm$^2$ skin area/hour for a time of from 17 to 27 hours, at an applied dose of from 2 to 20 mg minoxidil to said skin region, and with a period of from 16 to 30 hours before any subsequent reapplication of the formulation or (ii) subsequent to administration to the skin region of the release composition so that the sequentially applied minoxidil and release composition together mediate the dermal flux of minoxidil of at least 1.5 μg minoxidil/cm$^2$ skin area/hour for a time of from 17 to 27 hours, at an applied dose of from 2 to 20 mg minoxidil to said skin region, and with a period of from 16 to 30 hours before any subsequent sequential reapplication of the minoxidil and release composition.

In another aspect, the disclosure relates to a hair growth formulation kit, comprising a packaged minoxidil solution, as a first component, and a packaged aqueous release composition comprising glycerin and an emulsifying nonionic surfactant as a second component, and instructions instructing use of the first and second components in a method of inducing hair growth, according to the present disclosure.

Other aspects, features and embodiments of the disclosure will be more fully apparent from the ensuing description and appended claims.

BRIEF DESCRIPTION OF THE DRAWINGS

FIG. 1 is a graph showing mean flux, in micrograms/centimeter$^2$/hour (μg/cm$^2$/hr), plotted as a function of sample mid-time, in hours, for percutaneous absorption of minoxidil through ex vivo human scalp skin over 48 hours from a single application, (i) for a 5% minoxidil composition (Vitadil-5A), (ii) for a carrier composition (Nutrisol RM) followed by the 5% minoxidil composition (Vitadil-5A), and (iii) for a pre-mix 2:1 Vitadil-5A:Nutrisol RM formulation.

DETAILED DESCRIPTION

The present disclosure relates to the discovery that the heretofore conventional twice-daily administration of minoxidil, at a steady-state administration to the scalp of 15 mg of minoxidil twice-daily, is wholly unnecessary when minoxidil is administered according to a dosage regimen in which the amount of minoxidil administered daily is substantially reduced from that used in the conventional dosage regimen, but with a same or better therapeutic efficacy being achieved, when administering minoxidil with a carrier of a type as described in U.S. Pat. No. 7,749,489, either in mixture or in sequential administration with such carrier.

The dosage regimen of the present disclosure therefore achieves a remarkable advance in the art, enabling the amount of minoxidil to be utilized in a highly efficient manner at low dosages. Such dosage regimen was not contemplated from the disclosure of U.S. Pat. No. 7,749,489, and was found to be unexpectedly advantageous, from percutaneous absorption studies of minoxidil by the present inventor, who is also the inventor of said U.S. Pat. No. 7,749,489.

The dosage regimen of the present disclosure thus enables a once-daily administration of minoxidil at low dose, to achieve at least equivalent results to the dosage administrations conventionally used by the prior art. Such unexpectedly advantageous dosage regimen thus enables the overall amount of minoxidil administered to the scalp of the user to be dramatically reduced, but also enables a single daily effort to be dedicated to the minoxidil treatment, thereby substantially enhancing the prospect and probability of medication adherence by the user.

Thus, the disclosure relates in one aspect to a method of inducing hair growth by topical administration of minoxidil, said method comprising topically applying minoxidil to a skin region susceptible to induction of hair growth, wherein the applied minoxidil is administered to the skin region (i) in a formulation comprising a release composition that mediates a dermal flux of minoxidil of at least 1.5 μs minoxidil/cm$^2$ skin area/hour for a time of from 17 to 27 hours, at an applied dose of from 2 to 20 mg minoxidil to said skin region, and with a period of from 16 to 30 hours before any subsequent reapplication of the formulation or (ii) subsequent to administration to the skin region of said release composition so that the sequentially applied minoxidil and release composition together mediate said dermal flux of minoxidil of at least 1.5 µg minoxidil/cm² skin area/hour for a time of from 17 to 27 hours, at an applied dose of from 2 to 20 mg minoxidil to said skin region, and with a period of from 16 to 30 hours before any subsequent sequential reapplication of the minoxidil and release composition.

In such method, the release composition may comprise an aqueous composition including glycerin and an emulsifying non-ionic surfactant.

The formulation that is applied to the scalp of a user may thus may be constituted by mixing the release composition and the active ingredient minoxidil at the point of use, or the release composition and the active ingredient minoxidil may be provided in an already pre-mixed formulation that is applied by the user to the scalp.

When the formulation is constituted by mixing the release composition and the active ingredient minoxidil at the point of use, the minoxidil may be provided in an aqueous active ingredient composition, e.g., including glycol and alcohol, in addition to minoxidil and water, and such aqueous active ingredient composition may be mixed with the release composition to provide the formulation for use. The glycol in such active ingredient composition may be of any suitable type, and may comprise propylene glycol, or other glycol or polyol component. The alcohol in such active ingredient composition likewise may be of any suitable type, and may for example comprise ethanol or other alcohol species. The minoxidil in such active ingredient composition may be at any suitable concentration to provide the desired strength of minoxidil in the final formulation that is applied to the scalp of user, e.g., 2 wt % minoxidil, based on total weight of the formulation, 5 wt % minoxidil, based on total weight of the formulation, or other suitable weight percentage minoxidil in the formulation. In the circumstance in which the formulation applied to the scalp of user is provided in an initially pre-mixed formulation as manufactured, the active ingredient minoxidil may likewise be at any suitable concentration providing the desired strength for application, including the aforementioned 2 wt %, 5 wt %, or other weight percent concentrations, based on total weight of the formulation.

The formulation applied to the scalp may therefore comprise the release composition, together with minoxidil, glycol, and alcohol. Additional excipient ingredients may be incorporated in the formulation, including preservatives, stabilizers, antioxidants, carrier ingredients, fillers, solvents, propellants, etc., as desired in a specific formulation of the present disclosure.

In another aspect, the disclosure relates to a hair growth formulation kit, comprising a packaged minoxidil solution, as a first component, and an aqueous release composition comprising glycerin and an emulsifying non-ionic surfactant as a second component, and instructions instructing use of the first and second components in a method of inducing hair growth, in accordance with the aforementioned method of the present disclosure.

The aqueous release composition of the present disclosure may include glycerin and an emulsifying non-ionic surfactant, wherein the glycerin and surfactant are present at any suitable relative proportions in relation to one another that is effective to provide a dermal flux of minoxidil of at least 1.5 µg minoxidil/cm² skin area/hour for a time of from 17 to 27 hours, at an applied dose of from 2 to 20 mg minoxidil to the skin region. The surfactant may comprise a polysorbate material, such as polysorbate-80 or other suitable polysorbate component. In various embodiments, the aqueous release composition contains water, glycerin and polysorbate-80 components, in the following amounts: 40-70 weight percent water, 20-40 weight percent glycerin, and 5-15 weight percent polysorbate-80, wherein the weight percent of such ingredients are based on the total weight of the water, glycerin and polysorbate-80 in the release composition.

In other embodiments, the aqueous release composition may contain water, glycerin and polysorbate-80 in the following amounts: 55-60 weight percent water, 30-35 weight percent glycerin, and 8-12 weight percent polysorbate-80, where the weight percents of such ingredients are based on the total weight of the water, glycerin, and polysorbate-80 in the release composition. The release composition may also contain any suitable excipients, such as for example, any one or more of retinol, beta sitosterol, panthenol, cystine, biotin, polysorbate-20, DMDM hydantoin, methylparaben, and serenoa serrulata fruit extract. It will be appreciated that the release composition may be utilized without any excipients therein, in specific embodiments in the broad practice of the method of the present disclosure, and that in other embodiments, any one or more excipients may be incorporated in the formulation of such release composition.

In various embodiments, the aqueous release composition may have the following composition:

Release Composition

| | |
|---|---|
| water | 40-60 weight percent |
| glycerin | 20-40 weight percent |
| polysorbate 80 | 5-15 weight percent |
| optional additional ingredients (optional ingredients including, for example, retinol and/or other retinoid compound(s), betasitosterol, panthenol, DMDM-hydantoin, biotin, cystine, sabal seralata fruit extract and/or other saw palmetto compounds, and methyl paraben and/or other preservative(s)) | 0-3 weight percent |
| TOTAL | 100 weight percent |

The release composition may be provided in a two-package hair growth formulation, wherein the first package comprises the release composition, and the second package comprises minoxidil, e.g., in a solvent vehicle composition.

As an example, the minoxidil composition in various embodiments may comprise water, glycol, alcohol, and minoxidil, wherein the minoxidil composition may be mixed with the release composition at the point of use, or may be topically applied to the scalp after the release composition has been applied to the scalp, so that the minoxidil composition and the release composition are topically mixed in situ at the time of use.

The dosing regimen of the present disclosure may be carried out with minoxidil solutions that are mixed or sequentially administered with the release composition. For example, the minoxidil solution in a specific embodiment may contain minoxidil at a concentration of 5.097% by weight, based on the minoxidil solution weight (equivalent to 5.0% w/v), together with propylene glycol (52.803% by weight, based on weight of the solution), purified water (15.959% by weight, based on weight of the solution), and SD alcohol 40-B (26.141% by weight, based on weight of the solution).

As another example, the minoxidil solution may in another specific embodiment contain minoxidil at concentration of 2.208% by weight, based on weight of the solution (equivalent to 2.0% w/v), together with propylene glycol (22.870% by weight, based on weight of the solution), purified water (18.311% by weight, based on weight of the solution), and SD alcohol (56.611% by weight, based on weight of the solution).

In various embodiments, the applied dose of the minoxidil in the formulation of the disclosure in mixture with the aqueous release composition, or as sequentially applied following administration of the aqueous release composition, may be in a range of from 2.5 μL to 10 μL, depending on the size of the scalp that is treated. For example, user skull sizes may vary between extra small (XS) and extra-large (XL), and the corresponding dosages may be in a range of from 3 μL/cm$^2$ to 7.5 μL/cm$^2$.

In an illustrative minoxidil composition in a two-part formulation, the minoxidil composition may contain the following ingredients:

Minoxidil Composition

| | |
|---|---|
| water | 10-22 weight percent |
| propylene glycol or other glycol | 40-60 weight percent |
| ethanol or other alcohol | 20-30 weight percent |
| minoxidil | 1-10 weight percent |
| TOTAL | 100 weight percent |

In a specific two-part formulation, the release composition and the minoxidil composition may have the following ingredients and amounts.

Release Composition

| | |
|---|---|
| water | 56.23 weight percent |
| glycerin | 2.74 weight percent |
| methylparaben | 0.25 weight percent |
| panthenol | 0.01 weight percent |
| DMDM hydantoin | 0.20 weight percent |
| sabal seralata fruit extract | 0.01 weight percent |
| polysorbate-80 | 10.26 weight percent |
| beta sitosterol | 0.001 weight percent |
| biotin | 0.001 weight percent |
| cysteine | 0.001 weight percent |
| retinol | 0.30 weight percent |
| TOTAL | 100 weight percent |

Minoxidil Composition

| | |
|---|---|
| water | 19.96 weight percent |
| propylene glycol | 52.8 weight percent |
| ethanol | 26.14 weight percent |
| minoxidil | 5.1 weight percent |
| TOTAL | 100 weight percent |

The advantages and features of the disclosure are further illustrated with reference to the following non-limiting example.

EXAMPLE

A study was conducted to characterize the in vitro percutaneous absorption pharmacokinetics of minoxidil into and through ex vivo, human, scalp skin with male pattern baldness, using the Franz Finite Dose Model. The study was designed to evaluate the percutaneous absorption pharmacokinetics of 5% minoxidil solution (Vitadil-5A) both with and without a secondary application of Nutrisol RM, on ex vivo, human, scalp skin, with 3 replicant sections from each donor for each dosing regimen over a 48 hour dose period. At pre-selected times after dose application, the dermal receptor solution was removed in its entirety, replaced with fresh receptor solution, and an aliquot saved for subsequent analysis. In addition, the stratum corneum, epidermis and dermis were recovered and evaluated for drug content. The samples were analyzed for minoxidil content by high-performance liquid chromatography (HPLC).

The in vitro Franz human skin finite dose model has proven to be a reliable tool for the study of percutaneous absorption and the determination of the pharmacokinetics of topically applied drugs. The model uses ex vivo, human torso skin mounted in specially designed diffusion cells allowing the skin to be maintained at temperature and humidity that match typical in vivo conditions. A finite dose, e.g., 2 mg/cm$^2$-10 mg/cm$^2$, of a formulation is applied to the outer surface of the skin and drug absorption is measured by monitoring its rate of disappearance in the receptor solution bathing the inner surface of the skin. Data defining total absorption, rate of absorption, as well as skin content can be determined in this model. This methodology accurately predicts in vivo percutaneous absorption kinetics.

All reagents used in the study were of analytical reagent grade or better. The pre-mixed Vitadil/Nutrisol formulation was prepared in the testing laboratory prior to dosing at a ratio of 2:1 Vitadil-5A:Nutrisol RM. Dosing was conducted according to the following three administration regimens.

Regimen 1: A nominal 5 μL/cm2 of the minoxidil (Vitadil-5A) formulation was applied to the skin by pipette and evenly dispersed using a glass rod. The glass rod was retained for analysis of residual formulation to adjust minor corrections to the nominal dose.

Regimen 2: A nominal 2.5 μL/cm2 of the Nutrisol RM formulation was applied to the skin by pipette and evenly dispersed using a glass rod. The glass rod was not retained for analysis. Immediately following the Nutrisol application, 5 μL/cm2 of the minoxidil formulation was applied by pipette to the same skin sections. The applied dose was then evenly dispersed and rubbed into the skin surface using a glass rod. The glass rod was retained for analysis of residual formulation to adjust minor corrections to the nominal dose.

Regimen 3: A nominal 7.5 μL/cm2 of the pre-mixed 2:1 Vitadil-5A:Nutrisol RM combination was applied to the skin by pipette and evenly dispersed using a glass rod. The glass rod was retained for analysis of residual formulation to adjust minor corrections to the nominal dose.

The dermal receptor medium was normal phosphate buffered saline (pH 7.4±0.1) with 0.008% gentamicin sulfate (PBSg) solution when the diffusion cells were first mounted and for performance of the skin barrier integrity test. Following the barrier integrity test, the receptor solution was entirely replaced with 0.1×PBS with 0.1% Oleth-20 4 study conduct, used exclusively thereafter, and entirely replaced again following each sampling.

Percutaneous absorption was measured using the in vivo, human skin, Franz finite dose technique. Ex vivo, split thickness, human scalp skin with male pattern baldness, without obvious signs of skin disease or damage was used in the study. The scalp skin preparations were received sealed in a water impermeable bag and were frozen in continuous storage at approximately −20° C. Prior to use, the scalp skin preparation was thawed in approximate 37° C. water and then rinsed and distilled, deionized water (ddH$_2$O) to remove any inherent blood or other material from the surface. The skin was then manually dissected to remove any residual subcutaneous fat and approximately 50% of the dermal tissue from the underlying portion of the skin.

Skin from each donor was cut into multiple smaller sections large enough to fit on nominal 2.0 cm$^2$ static Franz diffusion cells. Each skin section was then mounted onto a diffusion cell.

The dermal receptor compartment was filled to capacity with PBSg. The epidermal chamber (also known as a chimney or donor compartment) was left un-occluded with exposure to the ambient laboratory environment. The cells were then placed within a rack system and attached to a water circulation system from which the receptor solution was stirred magnetically at a proximally 600 RPM, and its temperature was maintained to achieve a skin surface temperature of 32.0±1.0° C. One additional skin section per donor was prepared and underwent all study activities, but was not dosed, to serve as a negative sample control.

In the barrier integrity test, to ensure the barrier integrity of each skin section, the desorption water from the skin section was measured for trans-epidermal water loss (TEWL). A Delfin Vapometer® probe was activated, placed onto the skin surface, and the TEWL value was recorded. Skin sections that were determined to be unacceptable for dosing were reserved as non-dosed negative sample control cells, if needed.

The demographics of the Caucasian male donor individuals are set out below in Table 1.

TABLE 1

| Donor ID | Age | Integrity Test Results (g/m$^2$h) |
|---|---|---|
| S160152 | 66 | 16.44 ± 2.64 |
| S160330 | 76 | 20.83 ± 3.63 |
| S160235 | 69 | 13.02 ± 2.43 |

Dose administration sample collection was conducted as follows. Prior to administration of the topical test formulations to the skin section, a pre-dose (0 hour) sample was collected as the entirety of the receptor solution volume was withdrawn with an approximate 5 mL aliquot of the collected samples save for subsequent analysis. The receptor solution was replaced with a designated stock receptor solution of 0.1×PBS with 0.1% Oleth-20. The chimney was then temporarily removed from the Franz diffusion cell to allow full access to the epidermal surface of the skin. The skin sections were then dosed. Approximately 10 minutes after dose application, the donor compartment (chimney) of the Franz diffusion cells was replaced.

At the scheduled sampling time points (2, 4, 8, 12, 24, 32, and 48 hours post-dose), the receptor solution was removed in its entirety, refilled with stock receptor solution, and an approximate 5 mL aliquot of the collected samples saved for subsequent analysis.

After the last receptor sample was collected, with the donor compartment (chimney) of the diffusion cell assembly in place, the surface of the skin was washed with a solution of equal parts ethanol and water to collect un-absorbed formulation from the surface of the skin. The surface wash was performed using 2 successive 0.5 mL/cm$^2$ refluxing washes with a pipette. Each wash cycle consisted of at least 10 reflexes or until visible formulation had been washed from the skin. The two wash volumes from each donor cell were pooled to generate a single surface wash sample for that diffusion cell.

Following the surface washes, the skin was allowed to dry for no less than 10 minutes and then tape script to remove the stratum corneum (3M Transpore). Page stripping was accomplished by placing a ~1-inch strip of tape onto the skin surface, finger rubbed to affix, then gently removed. Up to 10 sequential strips were conducted on each skin section. All strips from a given section were pooled into a single file for subsequent processing. Sets of tape strips were extracted overnight in neat acetonitrile and later analyzed for minoxidil. Following tape stripping, the skin was dismounted from the cell and manually split into epidermis and dermis portions. Skin separation was performed by scoring the edge of the skin with a scalpel point or needle—0.4 steps. The epidermis is then peeled away from the dermis, falling onto itself for the center to avoid the surface coming into contact with the dermis, using needle-point forceps or scalpel blade. The dermis is then removed using a cork-borer sized to fit within the O-ring diameter. The skin sections were extracted overnight and equal parts ethanol and water, and were later analyzed for minoxidil content. All samples were stored at approximately −20° C. pending analysis.

In the sample analysis, drug concentrations were quantified and study samples using a high-performance liquid chromatography (HPLC) method, in which the solvent system consisting of 86% of water containing 0.1% formic acid and 14% methanol, was run through a Phenomonex Gemini C-18 110A column (50×3.0 mm, 3μ) at a flow rate of 0.5 mL/minute for the analysis of minoxidil by a UV detector for quantification.

If any sample was less than the Lower Limit of Detection (LLD), then that sample was identified for treatment as a non-data value. At the discretion of the study investigator, all values <LLD were identified for allocation as 0 values or as the actual value measured for calculating key parameters. Any suspected outliers were confirmed using the Dean and Dixon Outlier Test (Dean, R. B. and Dixon, W. J., Simplified statistics for small numbers of observations, Analytic Chemistry, 23 (4): 636-638).

Within a cell, if a given time-point value was declared a non-data value or was missing due to other reasons, that time-point value was considered for replacement with an interpolated value to calculate the relevant parameters. The interpolated value was calculated on a line that connects adjacent values, as follows: given 3 points (T1, A), (T2, B), and (T3, C) with (B) missing, where T=time, and A-C=measured data values, the estimated missing value (B) was determined as B=A−[((A−C)/[T1−T3])×([T1−T2])].

Concerning statistical evaluation, the replicants within donors were averaged and the standard deviation calculated for each key parameter. Within donor averages were then collated, and the across donor population mean with standard error was calculated. Differences between formulations were evaluated using the Student's T-test using p<0.05 as the measure of significance.

FIG. 1 is a graph of the test results, showing mean flux, in micrograms/centimeter$^2$/hour (μg/cm$^2$/hr), plotted as a function of sample mid-time, in hours, for percutaneous absorption of minoxidil through ex vivo human scalp skin over 48 hours from a single application, (i) for a 5% minoxidil composition (Vitadil-5A), (ii) for a carrier composition (Nutrisol RM) followed by the 5% minoxidil composition (Vitadil-5A), and (iii) for a pre-mix 2:1 Vitadil-5A: Nutrisol RM formulation.

Table 2 below shows the mean flux (μg/cm$^2$/hr) results (Across Donor Summary) for percutaneous absorption of minoxidil through ex vivo human scalp skin over 48 hours from a single application (mean±SE).

TABLE 2

| Time (hr)* | Vitadil-5A 5% Minoxidil Solution Lot 2151300 | Nutrisol RM (Lot 15316A) followed by Vitadil-5A 5% Minoxidil Solution (Lot 2151300) | Pre-Mix 2:1 Vitadil-5A:Nutrisol RM |
|---|---|---|---|
| 1.0 | 0.43 ± 0.42 | 0.15 ± 0.15 | 0.11 ± 0.10 |
| 3.0 | 1.57 ± 1.50 | 0.42 ± 0.41 | 0.34 ± 0.29 |
| 6.0 | 2.12 ± 1.62 | 0.87 ± 0.58 | 0.96 ± 0.57 |
| 10.0 | 2.02 ± 1.00 | 1.23 ± 0.54 | 1.47 ± 0.69 |
| 18.0 | 1.44 ± 0.26 | 1.53 ± 0.45 | 1.78 ± 0.74 |
| 28.0 | 1.13 ± 0.14 | 1.65 ± 0.51 | 1.76 ± 0.73 |
| 40.0 | 0.81 ± 0.07 | 1.36 ± 0.37 | 1.40 ± 0.50 |

*Time as midpoint between samples

Table 3 below shows total absorption and mass balance results (Across Donor Summary) for percutaneous absorption of minoxidil into and through ex vivo human scalp skin over 48 hours from a single application, mean±SE as percent of applied dose (percent sign) and total mass (μg/cm$^2$).

TABLE 3

| Parameter | Vitadil-5A 5% Minoxidil Solution Lot 2151300 | Nutrisol RM (Lot 15316A) followed by Vitadil-5A 5% Minoxidil Solution (Lot 2151300) | Pre-Mix 2:1 Vitadil-5A:Nutrisol RM |
|---|---|---|---|
| Total Absorption (μg/cm)$^2$ | 119.7 ± 38.2 | 125.5 ± 34.7 | 136.8 ± 52.9 |
| Dermis (μg/cm)$^2$ | 26.86 ± 4.48 | 49.40 ± 20.56 | 50.93 ± 15.16 |
| Epidermis (μg/cm)$^2$ | 36.12 ± 6.75 | 29.40 ± 13.42 | 38.79 ± 18.54 |
| Stratum corneum (μg/cm)$^2$ | 3.91 ± 1.76 | 2.37 ± 0.53 | 2.30 ± 0.41 |
| Surface Wash (μg/cm)$^2$ | 242.9 ± 8.8 | 221.6 ± 56.2 | 196.3 ± 58.0 |
| Total Absorption (%) | 24.20 ± 7.61 | 25.40 ± 7.03 | 27.63 ± 10.67 |
| Dermis (%) | 5.46 ± 0.94 | 10.03 ± 4.18 | 10.34 ± 3.08 |
| Epidermis (%) | 7.29 ± 1.34 | 5.97 ± 2.74 | 7.89 ± 3.81 |
| Stratum corneum (%) | 0.80 ± 0.36 | 0.48 ± 0.11 | 0.47 ± 0.08 |
| Surface Wash (%) | 49.28 ± 2.03 | 44.93 ± 11.36 | 39.84 ± 11.89 |
| Total Recovery (%) | 87.03 ± 5.21 | 86.81 ± 5.27 | 86.16 ± 4.64 |

The results indicated that minoxidil did absorb into and penetrate through ex vivo human scalp skin. The flux profiles of minoxidil from the three dosing regimens shown in FIG. 1 demonstrate that Vitadil-5A (5% minoxidil solution) provides an earlier peak flux (approximate 5 hours) than when it is combined with Nutrisol RM (peak flux at approximately 25 hours). The addition of Nutrisol RM to the Vitadil-5A (either by sequential dosing or in mixture with one another) delays and extends the percutaneous absorption of minoxidil.

Overall, mass balance (recovery) ranged from 86.2% to 87.0% and was similar across formulations and dosing regimens, as shown by the data in Table 2. Dermal content ranged from 5.46% (26.86 μg) to 10.34% (50.93 μg) and epidermal content ranged from 5.97% (29.4 μg) to 7.89% (38.79 μg) across formulations and dosing regimens.

The formulations and dosing regimens employing Nutrisol RM (either by sequential dosing or in mixture) with Vitadil-5A demonstrated meaningfully higher dermal content, with 49.40 and 50.93 μg of minoxidil in the dermis, as compared with the Vitadil-5A (5% minoxidil solution) alone, which resulted in 26.86 μg of minoxidil in the dermis. The mean Test to Reference ratio for the dermal content of the dosing regimens which used Nutrisol RM (either by sequential dosing or in mixture) with Vitadil-5A, as compared with the Vitadil-5A (5% minoxidil solution) alone, was approximate 1.73, indicating that the dermal content of the dosing regimens using Nutrisol RM was 1.73 fold higher than the 5% minoxidil solution alone.

Minoxidil delivered an accommodation with the Nutrisol RM demonstrated a delayed and extended percutaneous absorption of minoxidil. The absorption profile of the formulation establishes that the fundamentally different dosing regimen of the present disclosure, obviating the conventional twice a day application heretofore associated with minoxidil, can be used to achieve a sustained high level of minoxidil action on the scalp, while enabling a substantial reduction in side effects to be achieved by the markedly reduced release of minoxidil into the bloodstream associated with the release agent of the present disclosure.

While the disclosure has been set forth herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the disclosure as hereinafter claimed is intended to be broadly construed and interpreted, as including all such variations, modifications and alternative embodiments, within its spirit and scope.

What is claimed is:

1. A method of inducing hair growth by topical administration of minoxidil, said method comprising topically applying minoxidil to a skin region susceptible to induction of hair growth, wherein the applied minoxidil is administered to the skin region (i) in a formulation comprising a release composition that mediates a dermal flux of minoxidil of at least 1.5 μg minoxidil/cm$^2$ skin area/hour for a time of from 17 to 27 hours, at an applied dose of from 2 to 20 mg minoxidil to said skin region, and with a period of from 16 to 30 hours before any subsequent reapplication of the formulation or (ii) subsequent to administration to the skin region of said release composition so that the sequentially applied minoxidil and release composition together mediate said dermal flux of minoxidil of at least 1.5 μg minoxidil/cm$^2$ skin area/hour for a time of from 17 to 27 hours, at an applied dose of from 2 to 20 mg minoxidil to said skin region, and with a period of from 16 to 30 hours before any subsequent sequential reapplication of the minoxidil and release composition.

2. The method of claim 1, wherein the release composition comprises an aqueous composition comprising glycerin and an emulsifying non-ionic surfactant.

3. The method of claim 2, wherein the release composition comprises one or more excipients selected from the group consisting of retinol, beta sitosterol, panthenol, cystine, biotin, polysorbate-20, DMDM hydantoin, methylparaben, and serenoa serrulata fruit extract.

4. The method of claim 2, wherein the emulsifying non-ionic surfactant comprises polysorbate.

5. The method of claim 4, wherein the polysorbate comprises polysorbate-80.

6. The method of claim 1, wherein the release composition comprises 40-70 weight percent water, 20-40 weight percent glycerin, and 5-15 weight percent polysorbate-80, based on total weight of the release composition.

7. The method of claim 1, wherein the release composition comprises 55-60 weight percent water, 30-35 weight percent glycerin, and 8-12 weight percent polysorbate-80, based on total weight of the release composition.

8. The method of claim 1, wherein the release composition comprises the following ingredients:

| water | 40-60 weight percent |
| glycerin | 20-40 weight percent |
| polysorbate 80 | 5-15 weight percent |
| optional additional ingredients | 0-3 weight percent. | wherein the weight percent of all ingredients totals to 100 weight percent.

9. The method of claim 8, wherein the optional additional ingredients include one or more selected from the group consisting of retinol and/or other retinoid compound(s), betasitosterol, panthenol, DMDM-hydantoin, biotin, cystine, sabal seralata fruit extract and/or other saw palmetto compounds, and methyl paraben and/or other preservative(s).

10. The method of claim 1, wherein minoxidil is added in a minoxidil composition to the release composition to form the formulation, or is administered in the minoxidil composition to the skin region subsequent to administration thereto of the release composition, wherein the minoxidil composition comprises water, glycol, alcohol, and minoxidil.

11. The method of claim 10, wherein the glycol comprises ethylene glycol or propylene glycol.

12. The method of claim 10, wherein the alcohol comprises ethyl alcohol, propyl alcohol, or methyl alcohol.

13. The method of claim 10, wherein the minoxidil composition comprises the following ingredients:

| water | 10-22 weight percent |
| propylene glycol or other glycol | 40-60 weight percent |
| ethanol or other alcohol | 20-30 weight percent |
| minoxidil | 1-10 weight percent | wherein all weight percents total to 100 weight percent.

14. The method of claim 10, wherein the minoxidil composition comprises minoxidil at a concentration of 5.097% by weight, propylene glycol at a concentration of 52.803% by weight, purified water at a concentration of 15.959% by weight, and SD alcohol 40-B at a concentration of 26.141% by weight, wherein all weight percentages are based on total weight of the minoxidil composition.

15. The method of claim 10, wherein the minoxidil composition comprises minoxidil at a concentration of 2.208% by weight, propylene glycol at a concentration of 22.870% by weight, purified water at a concentration of 18.311% by weight, and SD alcohol 40-B at a concentration of 56.611% by weight, wherein all weight percentages are based on total weight of the minoxidil composition.

16. The method of claim 10, wherein the minoxidil composition comprises the following ingredients:

| water | 19.96 weight percent |
| propylene glycol | 52.8 weight percent |
| ethanol | 26.14 weight percent |
| minoxidil | 5.1 weight percent | wherein the weight percents of all ingredients total to 100 weight percent.

17. The method of claim 16, wherein the release composition comprises the following ingredients:

| water | 56.23 weight percent |
| glycerin | 2.74 weight percent |
| methylparaben | 0.25 weight percent |
| panthenol | 0.01 weight percent |
| DMDM hydantoin | 0.20 weight percent |
| sabal seralata fruit extract | 0.01 weight percent |
| polysorbate-80 | 10.26 weight percent |
| beta sitosterol | 0.001 weight percent |
| biotin | 0.001 weight percent |
| cysteine | 0.001 weight percent |
| retinol | 0.30 weight percent | wherein the weight percents of all ingredients total to 100 weight percent.

18. The method of claim 1, wherein the applied dose of minoxidil is in a range of from 2.5 µL to 10 µL.

19. The method of claim 1, wherein the applied dose of minoxidil is in a range of from 3 µL/cm$^2$ scalp area to 7.5 µL/cm$^2$ scalp area.

20. The method of claim 1, wherein the formulation is constituted at the point of use by mixing the release composition with an active ingredient composition comprising minoxidil.

21. The method of claim 20, wherein the release composition comprises an aqueous composition comprising glycerin and an emulsifying non-ionic surfactant.

22. The method of claim 20, wherein the active ingredient composition comprises an aqueous composition comprising glycol and alcohol ingredients in addition to said minoxidil.

23. The method of claim 20, wherein the release composition comprises an aqueous composition comprising glycerin and an emulsifying non-ionic surfactant, and wherein the active ingredient composition comprises an aqueous composition comprising glycol and alcohol ingredients in addition to said minoxidil.

24. The method of claim 1, wherein the formulation is pre-mixed, and comprises the release composition and minoxidil.

25. The method of claim 24, wherein the formulation further comprises water, glycol, and alcohol.

26. A hair growth formulation kit, comprising a packaged minoxidil solution, as a first component, and a packaged aqueous release composition comprising glycerin and an emulsifying non-ionic surfactant as a second component, and instructions instructing use of the first and second components in a method of inducing hair growth, according to claim 1.

* * * * *